United States Patent [19]
Kasahara et al.

[11] Patent Number: 5,557,351
[45] Date of Patent: Sep. 17, 1996

[54] APPARATUS FOR OBTAINING VISUAL IMAGES OF CORNEA CELLS AND METHOD FOR DISPLAYING IMAGING-POSITION AROUND CORNEA FOR THE APPARATUS

[75] Inventors: Tatsuya Kasahara; Yoichi Hamada; Yoshizo Ikegami, all of Nishinomiya, Japan

[73] Assignee: Konan Inc., Hyogo, Japan

[21] Appl. No.: 310,642

[22] Filed: Sep. 22, 1994

[30] Foreign Application Priority Data

Sep. 22, 1993 [JP] Japan ................................ 5-259445
Oct. 8, 1993 [JP] Japan ................................ 5-277714

[51] Int. Cl.⁶ .............................. A61B 3/10; A61B 3/14
[52] U.S. Cl. ...................... 351/221; 351/208; 351/211
[58] Field of Search ............................... 351/205, 206, 351/208, 211, 214, 216, 221, 212, 247

[56] References Cited

U.S. PATENT DOCUMENTS

5,436,679  7/1995  Ohtsuka et al. ................... 351/206

Primary Examiner—William L. Sikes
Assistant Examiner—Huy Mai
Attorney, Agent, or Firm—Koda and Androlia

[57] ABSTRACT

An apparatus for obtaining visual images of cornea cells, which allows magnified images of cornea cells to be easily obtained at required important sites of the cornea cells including a center site one by one by changing over the site, by leading the view axis of the subject and without requiring the decision of the operator in obtaining magnified images of cornea cells. Also, in order to allow a correct imaging site to be known, an imaging position mark is displayed at a correct position on the eyeball surface on the eye-front imaging screen of a TV camera. For illuminating through a slit an eyeball surface (2) and forming a magnified image of cornea cells of the subject part on an image-receiving surface (34) of a TV camera (35) via a magnification-imaging optical system based on the illumination light, a center view target and a plurality of view targets of required positions around the center view target are set by visible-light emitting diodes (27), (27₁) and these light-emitting diodes are arranged to be switchable one by one by a center lighting switch and a peripheral lighting-change switch. By this arrangement, an magnified image of the cornea cells of required positions can be easily obtained by leading the view of the subject.

8 Claims, 7 Drawing Sheets

APPARATUS FOR OBTAINING VISUAL IMAGES OF CORNEA CELLS AND METHOD FOR DISPLAYING IMAGING-POSITION AROUND CORNEA FOR THE APPARATUS

BACKGROUND OF THE INVENTION

1. Field of the Invention

The present invention relates to an apparatus for obtaining visual images of cornea cells, by which images of cornea endothelium cells of an eyeball of a subject person can be observed or photographed under magnification, and also relates to a method for displaying an imaging-position around the cornea for this type of apparatus for obtaining visual images of cornea cells.

For seeing influences of contact lenses or for medical examination and treatment before and after an operation of cataract, it is necessary to observe the state of cornea endothelium cells. Therefore, for observing or photographing under magnification cornea endothelium cells of an eyeball of a subject person, there have conventionally been used apparatus in which with an objective lens of a microscope of non-contact type or contact type with respect to the eyeball surface of the subject person, slit illumination light is applied toward an observation part obliquely of the eye axis, and its reflected light from the cornea is magnified, in which state the cornea endothelium cells can be observed, or in which apparatus an optimum imaging position where a TV camera or the like is focused on cornea endothelium is detected by the principle of the so-called triangulation method by detecting the position of the reflected light of the slit illumination light from the cornea endothelium, in which state the cornea endothelium cells of the subject part can be imaged by the TV camera or the like.

In these conventional apparatus, the focusing on the cornea endothelium has been accomplished in the following way. That is, the eye axis of the subject is aligned with the optical axis of the microscope by manually moving a microscope frame, which is the main body of the apparatus and which has a TV camera mounted thereon, up and down or right and left with the use of an operation member such as a joy stick so that an alignment indicator light is located at the center of the pupil of the eye on a monitor screen. In this state, the frame of the main body is moved back and forth also manually, so that the focusing is accomplished. However, in making observation or photographing with the above apparatus, there have been demands for observing or photographing under magnification not only the center portion but also various sites of the cornea including peripheral sites, depending on what is examined in the medical treatment. This being the case, it has been difficult to obtain successful images of sites other than the cornea center portion. Also, even when various measures are taken for obtaining such visual images, the view axis is led at discretion of the examiner, so that the imaging site would be difficult to standardize for operational reasons. As a result, visual images of important cornea sites could not be obtained easily.

Figure 8:
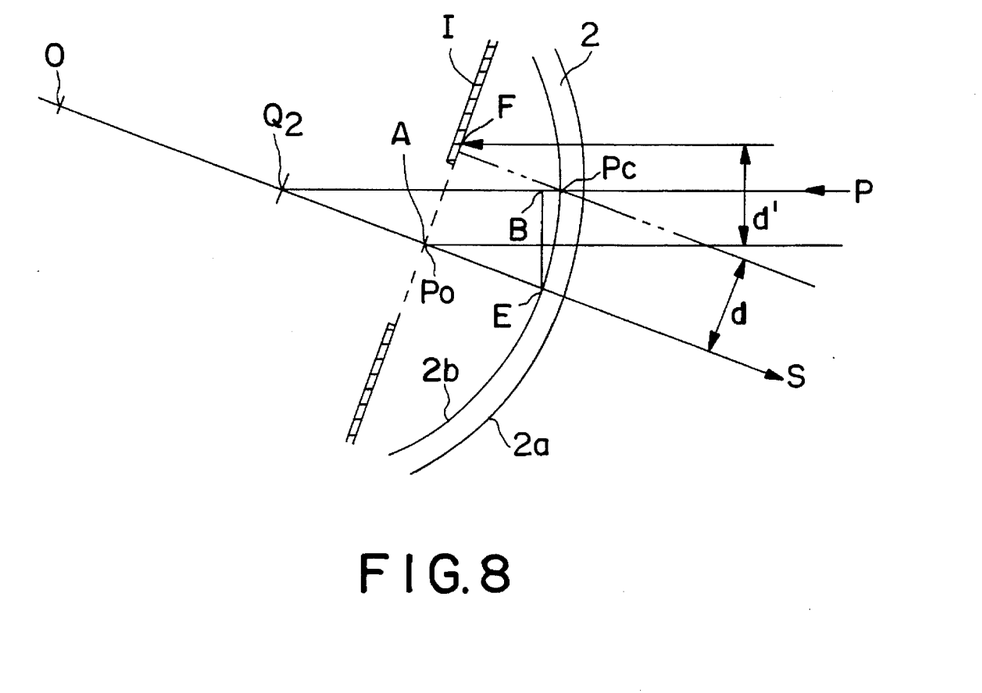
FIG. 8 is a view of the positional relation between the cornea-endothelium imaging position and the center of the pupil in obtaining a visual image of the periphery of a cornea.
Figure 9A:
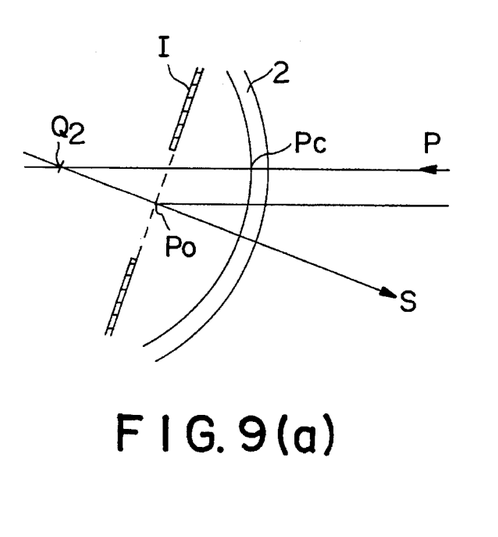
FIG. 9 is a view of the positional relation among the center of the pupil, the endothelium imaging position, and the monitor screen in fixedly viewing a view target.
Figure 9B:
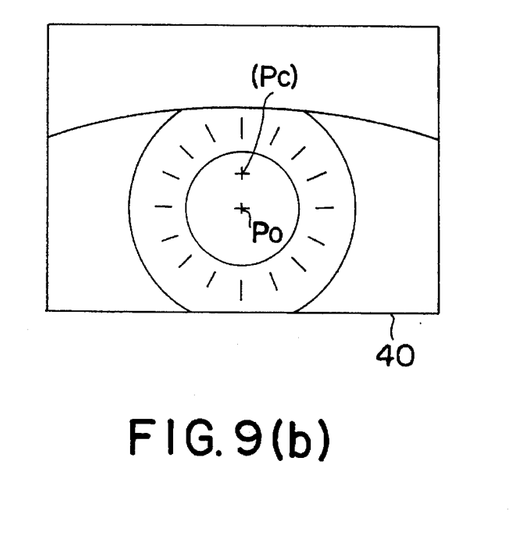

Further, in order to know an imaging site in obtaining visual images of cornea-peripheral sites, an image of eye-front part illuminated with the alignment indicator light applied to the eyeball surface is picked up by the TV camera, and the position where the imaging site is located generally in the cornea could be known by determining the position of the alignment indicator light from the eye-front image on the monitor with the eye directed along the eye axis, for example, with the eye fixedly viewing a peripheral view target. In this process, since the cornea is transparent and therefore could not be seen, the eye-front image would be observed by referencing the pupil or iris of the eye. Since the iris I is deeper than the cornea 2 as shown in FIG. 8, the cornea 2 moves to an extent more than the iris I as viewed in an imaging direction P. As a result, although an image is picked up at a cornea-endothelium imaging position $P_c$ which is away from a cornea-endothelium center E, i.e., an intersecting point E between the fixed-view direction S and a cornea-endothelium surface $2b$ by a distance d, yet the image looks from the screen as if it were picked up at a point away from the cornea center by a slight distance $AP_0$ (see FIG. 9 (b)). As a result, the correct position relative to the pupil center $P_0$ could not be displayed, as a problem. (In the figure, O is the eyeball rotation center, $P_0$ is the pupil center, and $Q_2$ is the cornea-endothelium center of curvature.)

The present invention has been developed in view of the above problems. A first object of the present invention is therefore to provide an apparatus for obtaining visual images of cornea cells, which can lead the view axis of a subject person without the need of decision of an operator (examiner), and which can easily obtain visual images of important cornea sites while it allows the imaging site to be moved (switched), and besides to provide an apparatus for obtaining visual images of cornea cells, which can obtain successful visual images of sites other than a center portion of the cornea.

Another object of the present invention is to provide a method for displaying an imaging position around a cornea in an apparatus for obtaining visual images of cornea cells, which method makes it possible to display an imaging-position mark at a correct position of the eyeball surface on an eye-front imaging screen of the TV camera, in obtaining or photographing a magnified image of cornea endothelium cells around the cornea of a subject eye by the apparatus for obtaining visual images of cornea cells, by leading the view axis of the subject by a doctor.

To accomplish the above objects, the present invention provides an apparatus for obtaining visual images of cornea cells, in which slit light from a slit illumination optical system is applied to the eyeball surface of the subject eye so that a magnified image of cornea cells of the subject part is observed or photographed by the cornea reflected light derived from the slit illumination light via a magnification-imaging optical system, characterized in that a plurality of view targets composed of visible-light sources and opposed to the subject eye are arranged to be switchable one by one by a center-position lighting switch and a peripheral-position lighting-change switch.

Desirably, the plurality of view targets of the apparatus are provided integrally with the magnification-imaging optical system.

Advantageously, the plurality of view targets are composed of a center view target to be positioned on the eye axis of the subject eye and peripheral view targets positioned approximately equal in distance to the center view target in directions of 4 o'clock, 6 o'clock, 8 o'clock, and 12 o'clock around the center view target.

Effectively, the apparatus for obtaining visual images of cornea cells comprises: an illumination optical system for illuminating through a slit an eyeball surface of a subject eye; a magnification-imaging optical system for forming a magnified image of the subject part on an image receiving surface of a TV camera, based on slit illumination light with which the eyeball surface has been illuminated; focusing-detection use receiving optics set in such a position as to receive cornea reflected light of the slit light via at least an objective lens; an eye-front imaging optical system for obtaining a visual image of the eye-front based on the eye-front illumination light; a plurality of view targets including a center view target set as opposed to the subject eye and composed of visible-light sources and arranged so as to be switchable for lighting; an alignment indicator light projection means for projecting alignment indicator light toward the subject eye; a cornea-reflected-light receiving means for receiving cornea reflected light of the alignment indicator light; and a means for moving the imaging system relative to the subject eye depending on output from the light receiving means so that the cornea reflected light of the alignment indicator light is brought to a specified position on a photoreceptor of the light receiving means, wherein the specified position on the photoreceptor can be moved in correspondence to lighting shift of the view targets.

Also, the present invention provides a method for displaying an imaging position around a cornea for use in the apparatus for obtaining visual images of cornea cells, in which slit light from the slit illumination optical system is applied to the eyeball surface of a subject eye and a magnified image of cornea cells of the subject part is observed or photographed by a TV camera from the cornea reflected light derived from the slit illumination light via the magnification-imaging optical system, while an eye-front image corresponding to the magnification-imaging position is photographed by the TV camera via the eye-front imaging optical system, characterized in that an imaging-position mark is displayed at a position calculated from both coordinates of the pupil of the eye on the eye-front imaging screen of the TV camera and coordinates of the cornea-cell imaging position on the eye-front imaging screen.

In the present apparatus, view targets composed of a plurality of visible-light sources and opposed to the subject eye are provided by a center-position lighting switch and a peripheral-position lighting changeover switch so as to be switchable for lighting one by one. By virtue of this arrangement, in observing or photographing a magnified image of cornea cells of a subject part via the magnification-imaging optical system based on reflected light from the eyeball surface illuminated through a slit by the illumination system, only selectively operating the switches allows the view axis of the subject to be led to a required position so that a visual image of a required important cornea site can be easily obtained.

In this arrangement, if the plurality of view targets are provided integrally with the magnification-imaging optical system, the subject eye can be led correctly toward a specified direction when the optical system of the imaging system, after starting operation from its standby position, has reached an imaging position.

In observing or photographing a magnified image of cornea cells of a subject part by leading the view axis of the subject person with this apparatus, if the view targets are provided by a center view target located on the eye axis of the subject person and peripheral view targets positioned approximately equal in distance from the center view target in the 4 o'clock, 6 o'clock, 8 o'clock, and 12 o'clock directions around the center view target, then visual images of standardized important sites of the cornea of the subject person can be easily obtained.

Also, in the apparatus for obtaining visual images of cornea cells, which comprises: an illumination optical system; a magnification-imaging optical system; focusing-detection use receiving optics for cornea reflected light of the slit light via at least an objective lens; an eye-front imaging optical system; a plurality of view targets including a center view target; an alignment indicator light projection means; a cornea-reflected-light receiving means for the alignment indicator light; and a means for moving the imaging system relative to the subject eye depending on output from the light receiving means so that the cornea reflected light of the alignment indicator light is brought to a specified position on a photoreceptor of the light receiving means, the specified position on the photoreceptor can be moved in correspondence to changeover of the lighting of the view targets. Accordingly, when the imaging site is switchedly moved, the apparatus can obtain high-accuracy visual images of the eye front at which the intersecting point of the imaging site illuminated with the alignment indicator light as well as of the subject part by making the imaging direction perpendicular to the cornea surface (cornea endothelium surface or cornea epithelium surface) of the imaging site.

In the method for displaying an imaging site around a cornea, in observing or photographing a magnified image of cornea cells of a subject part by a TV camera via the magnification-imaging optical system based on reflected light from the eyeball surface illuminated through a slit by the illumination system and meanwhile obtaining a visual image of the eye front by the TV camera via the eye-front imaging optical system, an imaging-position mark is displayed at a position calculated by an arbitrary means from two pieces of information, i.e., coordinates of the center of the pupil that can be taken out from the eye-front image of the TV camera and coordinates of a cornea-cell imaging position (known to the machine by the setting of the eye-front imaging optical system and the alignment position) that can be obtained by the movement of the imaging apparatus having the illumination system and the imaging system mounted thereon. By this arrangement, the method allows the correct imaging position, or which site of the cornea a visual image has been obtained at, to be displayed.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE PREFERRED EMBODIMENTS

Embodiments of the present invention are now described with reference to the accompanying drawings.

(Embodiment 1)

Figure 1:
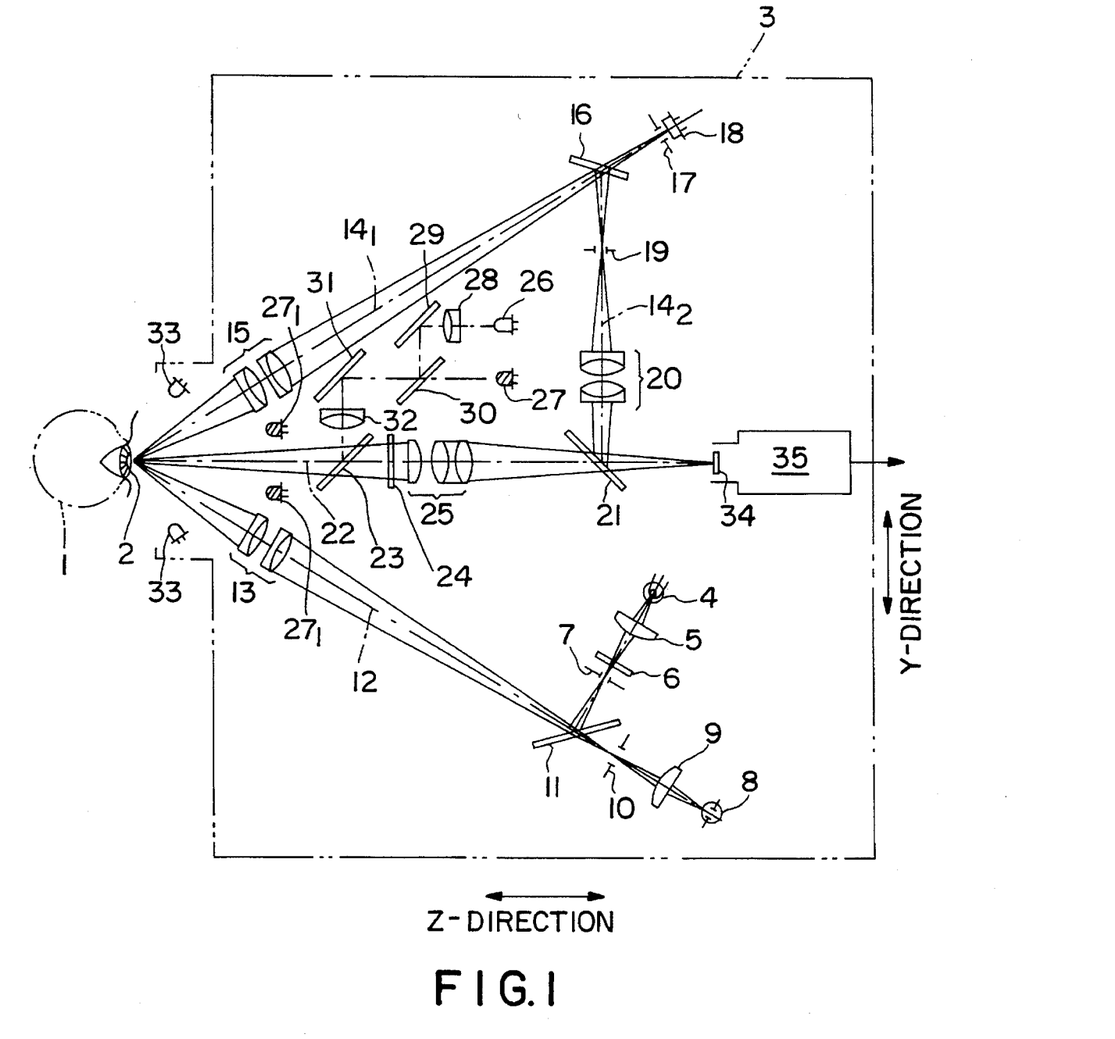
FIG. 1 is an optical path diagram of an embodiment of the present invention.
Figure 4:
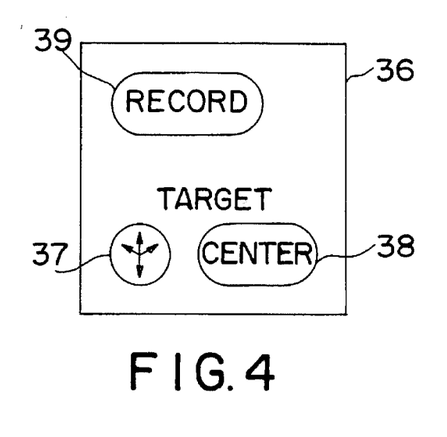
FIG. 4 is a view showing the operation buttons for switching the view target.

FIG. 1 is an optical path diagram of the embodiment. Visible-light emitting diodes $27_1$ for a plurality of peripheral view targets can be changed over by the operation buttons as shown in FIG. 4 so that the imaging site of the subject eye is moved and a visual image is obtained there.

In FIG. 1, there is shown an imaging system 3 comprising an illumination system for illuminating through a slit an eyeball surface 2 of a subject eye 1, a magnification-imaging optical system which is capable of observing or photographing under magnification an image of the subject part by a TV camera 35 based on slit illumination light with which the eyeball surface 2 has been illuminated, and view targets corresponding to observation sites of the subject eye, the imaging system 3 further comprising an eye-front imaging optical system which is so arranged that when the subject site moves along with alignment of the eye-front imaging optical axis to the subject eye, the alignment indicator light is projected on the subject eye, whereby the subject site by cornea reflected light is located in a specified position so that the cornea reflected light is formed into a visual image by the TV camera 35. The imaging system 3 will be moved in three directions, i.e., an X-direction, which orthogonally crosses an optical axis 22 of the eye-front imaging optical system and which is vertical to the paper surface of the figure, a Y-direction, which is an up and down direction of the paper surface, and a Z-direction, which is the direction of the eye-front imaging optical system optical axis 22, by unshown drive means, respectively.

As illumination sources for the subject part of the eyeball surface 2, there are provided an illumination lamp 4 used for focusing of the magnification-imaging optical system and a strobe discharge tube 8 used for photographing cornea endothelium cells under magnification. In order that rays of light emitted by the respective illumination sources illuminate the cornea 2, which is an observation surface of the subject eye 1, from an illumination optical axis 12 via a projection lens 13 at a specified angle obliquely with respect to the eye axis, the strobe discharge tube 8 is located in a specified position on the illumination optical axis 12 while the illumination lamp 4 is located on an optical axis perpendicular to the illumination optical axis 12 via a half mirror 11 on the illumination optical axis 12.

Further, for the light emitted by the illumination lamp 4, at a position where it is focused by a condenser lens 5 there is provided a detection-use slit aperture 7 having a specified small width and corresponding to a slit aperture 17 in front of later-described focusing-detection use receiving optics 18. Meanwhile, for the light emitted by the strobe discharge tube 8, at a position where it is focused by a condenser lens 9 there is provided an imaging-use slit aperture 10 having a specified rather large width and being purposed for allowing a wider view field imaging, in which case a visible-light cut filter 6 is further provided on the optical axis of the illumination lamp 4 forward of the detection-use slit aperture 7. Thus, only infrared light out of the light of the illumination lamp 4 is reflected by the half mirror 11, which reflects infrared light and transmits visible light, and projected onto the cornea 2, while visible light of the strobe discharge tube 8 is transmitted by the half mirror 11 and applied to the eyeball surface 2.

In the optical system for imaging the eye-front part, there are disposed a half mirror 23, a visible-light cut filter 24, an eye-front imaging lens 25, and a half mirror 21 crossing the optical axis 22 at 45° at their respectively specified positions on the eye-front imaging optical system optical axis 22 to be positioned on the eye axis in this order from the front. With this arrangement, an eye-front image is formed by the eye-front imaging lens 25 on a CCD photoreceptive surface 34 in front of the TV camera 35 located rearward, while near-infrared light as the alignment indicator light for alignment of the subject part that moves while serving also for the later-described alignment of the apparatus is projected to form a visual image. Also, on specified positions in front part of the imaging system 3 with the eye-front imaging optical system optical axis 22 interposed therebetween, infrared-light emitting diodes 33, 33 are disposed so as to illuminate the eye front part from outward of the optical paths of the illumination optical system and the later-described magnification-imaging optical system. The infrared-light emitting diodes 33, 33 will light in obtaining an eye-front image.

Also, on the side opposite to the illumination optical axis 12 of the illumination optical system with the eye-front imaging optical system optical axis 22 interposed therebetween, there is provided a magnification-imaging optical system which, receiving cornea-reflected light of the oblique slitted illumination light from the illumination lamp 4 or the strobe discharge tube 8 to the eyeball surface 2, forms an image of cornea endothelium cells of the subject part on an image receiving surface (CCD photoreceptive surface) 34 of the TV camera 35, thus allowing the image of the cornea endothelium cells to be observed or photographed under magnification. When the cornea endothelium image is formed on the image receiving surface 34 of the TV camera 35 in a focused state, the focusing-detection use receiving optics 18 set in a position resulting from extending an optical axis $14_1$ that passes through an objective lens 15 of the optical system detects cornea endothelium reflected light (or cornea epithelium reflected light) that moves in front of the receiving optics 18 as the imaging system 3 moves forward.

In more detail, at specified positions on an optical axis $14_1$ of the magnification-imaging optical system located symmetrically with the illumination optical axis 12 with respect to the eye-front imaging optical axis 22, an objective lens 15 is disposed on the eyeball surface side and a half mirror 16, which transmits infrared light and reflects visible light, is disposed at a specified distance from the objective lens 15, so as to cross the optical axis 14₁ at a specified angle and thereby to bend an image ray of reflected light of the above illumination light derived from the eyeball surface 2 so that the image ray will orthogonally cross the optical axis 22 of the eye-front imaging optical system at a specified position generally on the axis line. The image ray reflected by the half mirror 16 passes on the optical axis 142 through a field diaphragm 19 and a magnifying lens 20, which are located on an intermediate image-forming plane. Then, visible light of magnification-imaging-use slit light by the strobe light out of the magnified image ray is totally reflected by a half mirror 21 crossing the eye-front imaging optical system optical axis 22 at 45°, so as to be bent and incident on the image receiving surface (CCD photoreceptive surface) 34 of the TV camera 35 provided on the eye-front imaging optical system optical axis 22. Meanwhile, infrared light of the slit light for detection of an optimum imaging position (for use of focusing detection) is incident on the focusing-detection use receiving optics 18 provided at a position where the image of the cornea reflected image ray is formed by the objective lens 15, the position resulting from extending the optical path on the optical axis 14₁.

By virtue of the above arrangement, when the cornea endothelium image is formed on the image receiving surface 34 of the TV camera 35 by the objective lens 15 and the magnifying lens 20 in a focused state, slitted endothelium reflected light is better separated from adjacent epithelium reflection by the slit aperture 17 elongated in the longitudinal direction of the cornea reflected image in front of the focusing-detection use receiving optics 18. At the same time, by detection-use slit light that is incident on the receiving optics 18 as it is reduced in width by the slit aperture 7 located at the position where the light emitted by the illumination lamp 4 is focused, cornea endothelium reflected light can be detected by the receiving optics 18 with high positional accuracy and reliability, so that an optimum imaging position (focusing position) for the apparatus can be detected.

Figure 3:
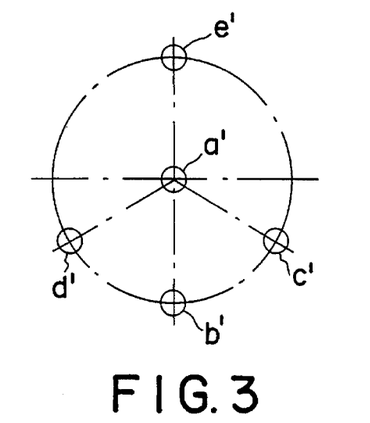
FIG. 3 is an arrangement view of the view targets corresponding to the observation or photographing sites as it is viewed from the subject side.

Further, the target light (visible light) for presenting a center target a' (see FIG. 3) to the subject and near-infrared light, which serves as the alignment indicator light for making the eye axis and the optical axis 22 coincident with each other and which serves also for detection of the subject part, are each made to be incident on the half mirror 23 on the eye-front imaging optical system optical axis 22 from the lateral direction perpendicular to the optical axis 22, so that these rays of light are advanced on the eye-front imaging optical system optical axis 22 so as to be incident on the eyeball surface 2. Also, in order to obtain visual images of specified standardized important cornea sites by leading the eye of the subject and thereby moving the imaging site of the cornea, it is arranged that visible light is applied toward the subject eye in the outer circumferential direction of the eye-front imaging optical system optical axis 22 to present to the subject a target c' located at 4 o'clock, a target b' located at 6 o'clock, a target d' located at 8 o'clock, and a target e' located at 12 o'clock (see FIG. 3), each at an equal distance from the center target a' around the center target a' located which is to be positioned on the eye axis of the subject eye.

In more detail, at specified positions beside the eye-front imaging optical system, a near-infrared light emitting diode 26, which is the alignment indicator light, and a visible-light emitting diode 27, which is the target light, are disposed so that the optical axes of their respective rays will be parallel to the eye-front imaging optical system optical axis 22. By this arrangement, the near-infrared light from the near-infrared light emitting diode 26 passes a condenser lens 28, a mirror 29, a near-infrared-light reflecting and visible-light transmitting mirror 30, a mirror 31, and a condenser lens 32, and is reflected by the reflective surface of the half mirror 23 so as to be incident on the eyeball surface 2 on the eye-front imaging optical system optical axis 22. Moreover, the visible light from the visible-light emitting diode 27 passes the near-infrared-light reflecting and visible-light transmitting mirror 30 and, like the near-infrared light, passes the mirror 31, the condenser lens 32, and the half mirror 23, advancing on the eye-front imaging optical system optical axis 22 so as to be incident on the eyeball surface 2. Further, at specified positions in the directions of 4 o'clock, 6 o'clock, 8 o'clock, and 12 o'clock as viewed from the subject at an approximately equal distance from the optical axis 22 around the optical axis 22, visible-light emitting diodes 27₁ are disposed so as to face the subject eye 1, respectively.

Figure 2:
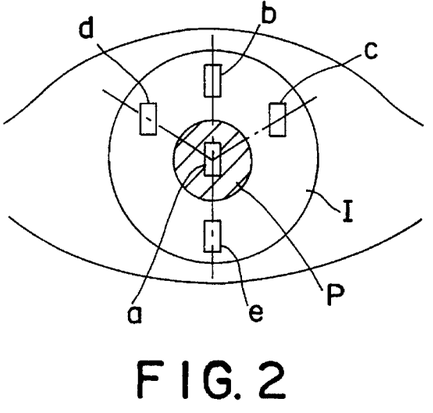
FIG. 2 is a front view of an eye front showing observation or photographing sites of a cornea.

Also, in the imaging system 3, by operating operation buttons, which are lighting switches on a button base 36 (see FIG. 4) of an unshown operation unit, for example, by merely pressing a record button 39, the center target a' (see FIG. 3) is lit, where an image of a site a of the center of the pupil P in the iris I of the eye-front part of FIG. 2 showing an observation or photographing site of the subject who is fixedly viewing the center target a' is obtained so that an eye-front image resulting from imaging the alignment indicator light or a magnified image of cornea endothelium cells at the imaging site a can be observed or photographed on the monitor connected to the TV camera 35. Then, each time a change button 37 is pressed, the target (target light) changes over in the order of, for example, a'→b'→c'→d'→e'→a' (see FIG. 3). In this operation, when the subject fixedly views any target (target light) other than the target a' located at the standard position, the observation or imaging site of the subject eye becomes vertically symmetrical with the target with respect to the pupil center site a. That is, when the subject fixedly views the target b' in the 6 o'clock direction below the center standard target a', the observation or imaging site is b in the 12 o'clock direction above the pupil P_u; when the subject fixedly views the target c' in the 4 o'clock direction, the observation or imaging site is c in the 2 o'clock direction; when the subject fixedly views the target d' in the 8 o'clock direction, the observation or imaging site is d in the 10 o'clock direction; and when the subject fixedly views the target e' in the 12 o'clock direction, the observation or imaging site is e in the 6 o'clock direction (see FIG. 2).

Also, correspondingly to the operation of the change button 37, the imaging position is displayed on an unshown control panel or monitor screen. Accordingly, a proper position is selected by the operation of the change button 37, and the record button 39 is pressed, whereby the selected position can be imaged. Further, in the operation of the change button 37, when a center button 38 is pressed at any step, the target will return to the standard position a'.

In the present apparatus, a specified position on the light receiving element (CCD photoreceptor 34 in the figure) for receiving cornea reflected light of the alignment indicator light is arranged to be movable from the center position, which is the standard position, in correspondence to a change in the lighting of the target (target light). With this arrangement, for changing the imaging site, the imaging system 3 is moved in the X- and Y-direction so that the imaging direction becomes perpendicular to the cornea endothelium surface of the imaging site, whereby the alignment indicator light is led to a specified position on the image receiving surface, which is the alignment position. Then the imaging system 3 is moved in the Z-direction while the alignment indicator light is maintained at the specified position. When the imaging system 3 has reached the imaging position, the subject eye can be led in a specified direction correctly, so that a visual image of the subject part can be obtained with high positional accuracy.

Figure 5:
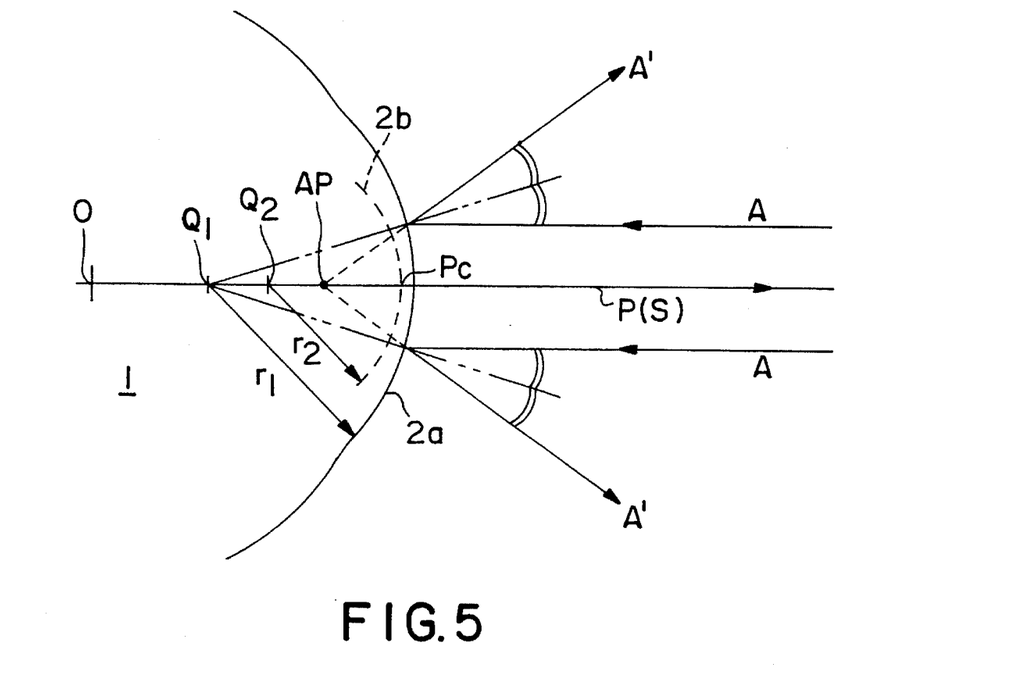
FIG. 5 is a view of the relation among the imaging site, the alignment indicator light position, and the fixed view direction in obtaining a visual image of the center of a cornea.
Figure 6:
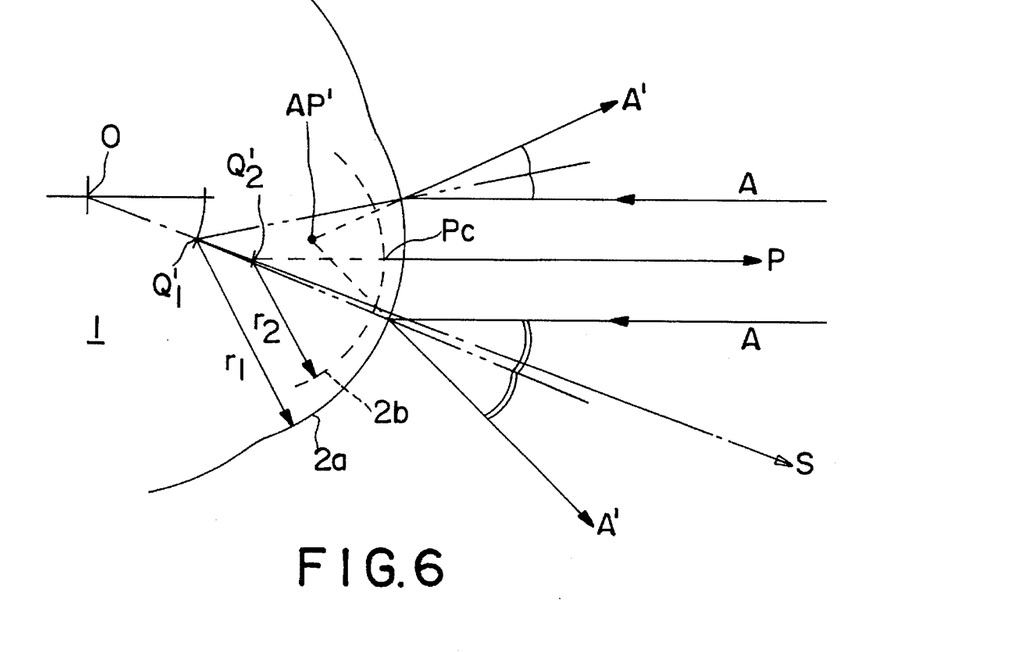
FIG. 6 is a view of the relation among the imaging site, the alignment indicator light position, and the fixed view direction in obtaining a visual image of the periphery of a cornea.

FIGS. 5 and 6 illustrate optical paths showing the correlation among the imaging site of the cornea surface, the alignment indicator light position, and the fixed view direction, with more or less emphasis. FIG. 5 shows a case where the subject person fixedly views the target (target light) a', i.e., fixedly views the direction of imaging optical axis, where a visual image of cornea endothelium is obtained. In this case, a cornea epithelium center of curvature $Q_1$, a cornea endothelium center of curvature $Q_2$, and an alignment indicator virtual image AP are aligned in a straight line as viewed in the imaging direction P. That is, the imaging direction P, which is the direction of the imaging optical axis, coincides with the fixedly viewing direction S and also orthogonally crosses a cornea epithelium 2a surface with a radius $r_1$ taking the cornea epithelium center of curvature $Q_1$ as its center, and a cornea endothelium 2b surface with a radius $r_2$ taking the cornea endothelium center of curvature $Q_2$. When the rays of alignment indicator light A, A are reflected by the cornea epithelium 2a surface, an alignment indicator virtual image AP which results at an intersecting point between the rays of alignment indicator reflected light A, A reflected symmetrically with respect to a line that connects the reflection point and the cornea epithelium center of curvature $Q_1$ (two-dotted chain line in the figure) is positioned on the imaging optical axis. Then, at the imaging center $P_c$ showing the imaging site a of the cornea endothelium 2b, since the cornea endothelium 2b orthogonally crosses the imaging direction P, a visual image of the site a can be obtained with high accuracy.

FIG. 6 shows a case where the cornea endothelium can be imaged with the subject fixedly viewing the target b' or others around the center target (target light) a', which is the standard position. In this case, the eyeball 1 of the subject rotates around an eyeball rotation center O, and its fixedly viewing direction S is toward a direction crossing the imaging direction P while the rays of alignment collimated light A, A form a virtual image in the direction of the cornea epithelium center of curvature, whether upper or lower. However, an alignment indicator virtual image AP' due to the cornea epithelium center of curvature $Q_1'$, the cornea endothelium center of curvature $Q_2'$, and the alignment indicator light A, A is not positioned in a straight line as viewed in the imaging direction P. Accordingly, in obtaining the alignment indicator virtual image in accordance with the alignment position, if the alignment position were the same as in obtaining a visual image of the center site, the cornea endothelium radius $r_2$ would be smaller than the cornea epithelium radius $r_1$ so that the imaging direction P would be, indeed perpendicular to the cornea epithelium 2a surface, but not perpendicular to the endothelium 2b surface, resulting in an unsuccessful image of endothelium. With the invention apparatus, which is so arranged that the specified position on the photoreceptor, which is the alignment position, is movable in correspondence to the movement of the lighting of the view targets, the cornea endothelium center of curvature $Q_2'$ is imaged at a position as viewed in the imaging direction P with the view line S applied in the direction of the imaging optical axis. In this way, the imaging direction P is made to orthogonally cross the cornea endothelium 2b surface at the imaging center $P_c$ so that a successful visual image of the subject part can be obtained.

Also, in the above-described apparatus for obtaining visual images of cornea cells, a successful visual image of the cornea endothelium can be obtained with high accuracy when it is imaged with the subject fixedly viewing the view target at a required position around the standard view target. However, in recording both visual images of an eye-front image showing the imaging site and a magnified cornea endothelium image of the subject part, it is desirable to eliminate any difference in image quality of the two.

In more detail, when the alignment indicator light is projected on the subject part and the imaging system is moved forward with the cornea reflected light spot maintained at a specified position on the image-receiving surface of the TV camera, which is an image receiving element, the eye-front observation (imaging) optical system becomes a dark optical system due to the need of obtaining a deeper focusing depth, owing to change in the observation distance. This being the case, two images different in brightness, i.e., an image for recording the eye-front image by the optical system and an image for recording a magnified image of the cornea endothelium by the magnification-imaging optical system, which uses strobe light of cornea cells that involve high-speed movements such as fixed-view small movements, both need to be received by one image-receiving element with good image quality.

For this reason, in the above apparatus, it is preferable that the TV camera 35 is provided with a gain changeover means, wherein the gain (sensitivity) of the TV camera 35 is increased by an epithelium detection signal derived from the focusing-detection use fiber optics 18 so that an eye-front image at which the alignment light spot of the subject site is positioned is recorded, and wherein after the recording the gain (sensitivity) of the TV camera 35 is returned back, so that a magnified image of cornea endothelium of the subject part is recorded with an endothelium detection signal. By this arrangement, two images of an eye-front image and an magnified image of cornea endothelium, which are different in brightness, can be received by the TV camera 35 with good image quality and recorded successfully by the recording means provided in the apparatus.

(Embodiment 2)

Next described is an embodiment of the method for displaying an imaging-position around a cornea for this type of apparatus for obtaining visual images of cornea cells, that is, an apparatus so arranged that slit light from the slit illumination optical system is applied to the eyeball surface of a subject eye and a magnified image of cornea cells of the subject part is observed or photographed from cornea reflected light of the slit illumination light through the magnification-imaging optical system, while an eye-front image corresponding to the imaging position of the above magnified image is obtained by the TV camera through the eye-front imaging optical system.

For this purpose, the apparatus for obtaining visual images of cornea cells is capable of observing or photographing an eye-front image with an imaging position mark M displayed as described later, or a magnified image of cornea endothelium cells at an imaging site, on a monitor 40 connected to the TV camera 35 of the imaging system 3 (see FIG. 1), by operating the operation buttons (see FIG. 4), which are lighting switches of an unshown operation unit, to change over the view target (target light) one by one, and thereby leading the view line of the subject person to obtain a visual image of the observation or photographing site of the subject eye that is fixedly viewing a center or peripheral required view target.

Now described is the displaying of an imaging site when a magnified image of cornea cells of a subject part around the cornea is obtained by the above-described apparatus for obtaining visual images of cornea cells.

Figure 7:
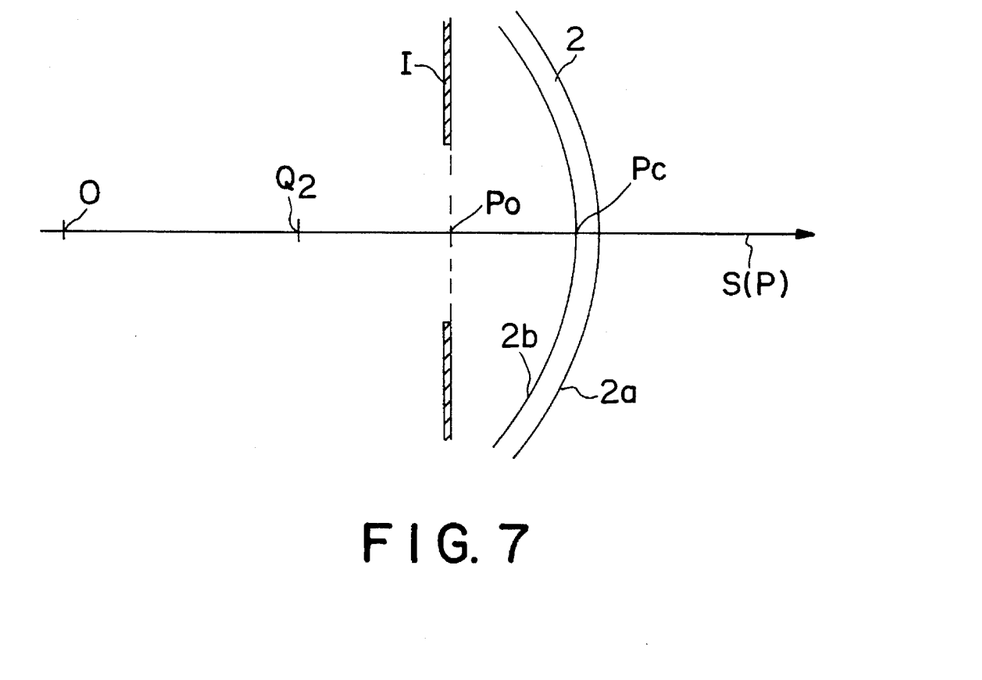
FIG. 7 is a view of the positional relation between the cornea-endothelium imaging position and the center of the pupil in obtaining a visual image of the center of a cornea.

FIG. 7 shows the positional relation between the cornea endothelium imaging position $P_c$ and the pupil center $P_o$ when an image of the cornea center is obtained with the subject person fixedly viewing the center view target of the imaging apparatus. FIG. 8 shows the positional relation between the cornea endothelium imaging position $P_c$ and the pupil center $P_o$ when an image of cornea peripheral part is obtained with the subject person fixedly viewing the aforementioned required peripheral view target (target light $27_1$).

In FIG. 7, the subject is viewing in the direction S with a fixedly view on the center view target, and the eye-front imaging optical system is automatically aligned so as to be directed toward the cornea endothelium center of curvature $Q_2$, where the eyeball rotation center O, the cornea endothelium center of curvature $Q_2$, the pupil center $P_o$, and the cornea endothelium imaging position $P_c$ are aligned in a straight line with the imaging direction P, in which state an visual image of cells at the cornea endothelium imaging position and an eye-front image immediately before the imaging optical system are obtained and recorded.

When the peripheral part of the cornea is imaged, a peripheral view target (for example, the view target in the 4 o'clock direction) is lit (the center view target is off), and the view of the subject is led so that the subject fixedly views the view target, with the result that the subject views in the direction S inclined from the horizontal direction as shown in FIG. 8, the imaging optical system moves in three directions of X-, Y-, and Z-directions while keeping in the horizontal direction as in the foregoing case, so as to be directed toward the cornea endothelium center of curvature $Q_2$, in which state a visual image of cells at the cornea endothelium imaging position $P_c$ and an eye-front image with the pupil center $P_o$ located below the imaging direction P are obtained and recorded. When the view is shifted toward a peripheral view target from the center view target, a movement BE of the cornea endothelium center E as viewed from the imaging direction P is magnified to $Q_2E/Q_2P_o$ times a movement $AP_o$ of the pupil center $P_o$. Then, a distance d between the cornea endothelium imaging position $P_c$, which is the intersecting point between the cornea endothelium 2b and the imaging direction P, and the fixedly viewing direction S is a distance of a position symmetrical to BE with respect to points E and $P_c$, and the same distance as BE. Therefore, if BE=d', then the imaging position mark can be displayed at a correct position with respect to the pupil center $P_o$ by marking a position (F) which is d' away from the pupil center $P_o$ in the direction of cornea endothelium imaging position $P_c$ as viewed in the imaging direction P.

Figure 11A:
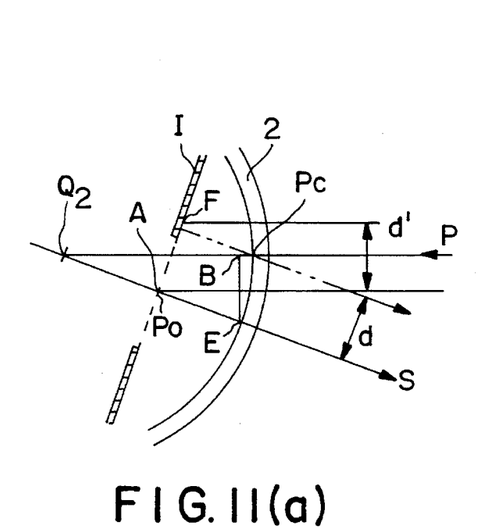
FIG. 11 is a view of the positional relation between the mark position of the iris and the monitor screen, where an imaging position mark is displayed on the monitor screen by applying the BE=d' as a distance from the pupil center $P_0$.
Figure 11B:
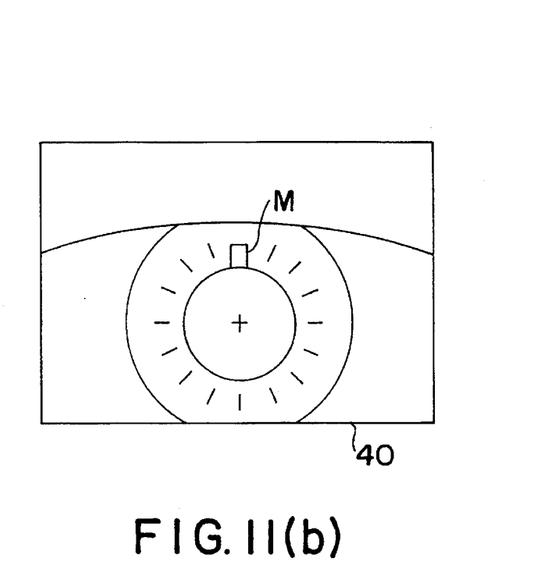
Figure 12:
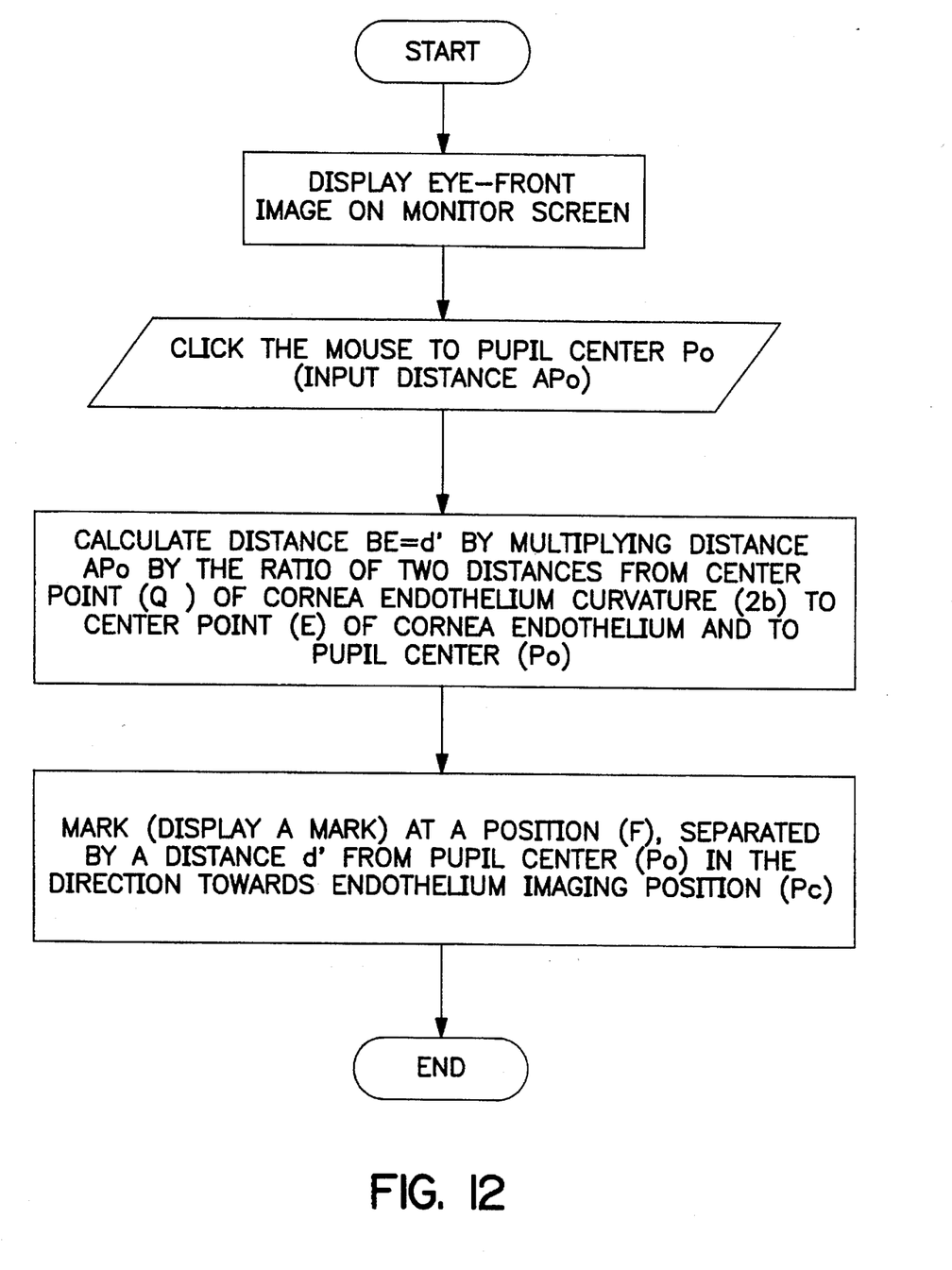
FIG. 12 is a flow chart showing the operation of the embodiment.

Nextly, the process in which the imaging position mark is displayed in the eye-front image on the monitor is described with reference to FIGS. 9 to 11, which are positional relation diagrams among the pupil center $P_o$, the endothelium imaging position $P_c$, and the monitor screen 36, and to FIG. 12, which is a flow chart showing the system operation.

First, in the imaging system 3, in order that the subject is made to fixedly view a required view target (target light), the visible-light emitting diode $27_1$ at a specified position in the 6 o'clock direction is lit and the view of the subject is led so that the subject fixedly views the view target. Then, the eye-front imaging optical system moves in the three directions of the X-, Y-, and Z-direction while maintaining in the horizontal direction, where the apparatus is automatically aligned so as to be directed toward the direction of the cornea endothelium center of curvature $Q_2$, in which state a cell image at the cornea endothelium imaging position $P_c$ and an eye-front image are obtained and recorded. In this case, the eye-front image of the subject eye as shown in FIG. 9A, in which the subject eye fixedly views the view target in the 6 o'clock direction to view the direction S, is displayed on the monitor screen 36 attached to the circuit on the output side of the TV camera 35, and looks as in FIG. 9B. The cornea endothelium imaging position $P_c$ in this case is located at a position in the 12 o'clock direction above the pupil center $P_o$ on the screen 36, at a distance smaller than the distance (the foregoing d) from the actual pupil center $P_o$.

Figure 10A:
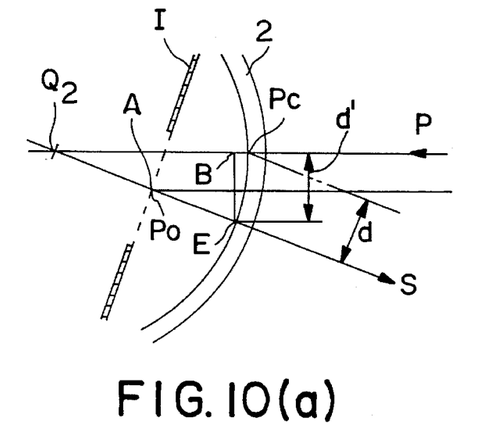
FIG. 10 is a view of the positional relation between the center of the pupil and the monitor screen, where BE=d' is calculated by clicking the mouse to the center of the pupil of an eye-front image and inputting a distance $AP_0$ between the pupil center $P_0$ and the eye-front imaging direction P.
Figure 10B:
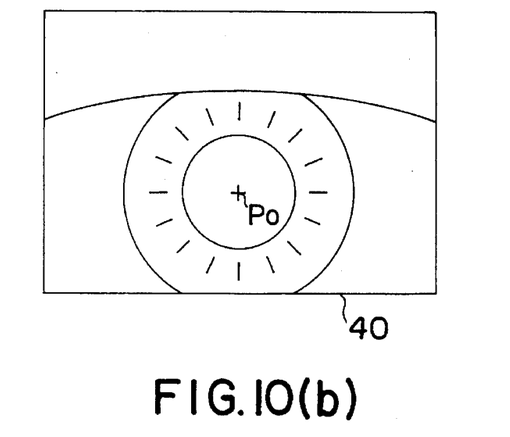

In the subsequent process, the distance of $AP_o$ as shown in FIG. 10A is inputted into an unshown arithmetic unit by clicking the mouse to the pupil center $P_o$ of the eye-front image on the monitor screen 36. Then, a distance resulting from magnifying the distance $AP_o$ by a ratio of a distance $Q_2P_o$ from the cornea endothelium center of curvature $Q_2$ to the iris I to another distance $Q_2E$ to the cornea endothelium, i.e., a distance BE=d' derived from $AP_o \times Q_2E/Q_2P_o$ is calculated (see FIG. 10).

With the use of the calculated d', an imaging position mark M of, for example, square shape is displayed (marked) at a position (F) which is d' away from the pupil center $P_o$ in the direction of the cornea endothelium imaging position $P_c$. This makes it possible to know which position of the cornea endothelium has been imaged, or the correct imaging position of the magnified image of cornea endothelium cells (see FIGS. 11A and B).

In addition, for inputting the distance of $AP_o$ as shown in FIG. 10A, instead of clicking the mouse to the pupil center, the imaging position indication mark M may be automatically displayed in the eye-front image on the monitor screen 36 by automatically detecting the pupil center $P_o$ to input the distance of $AP_o$, without doing the clicking operation. Also, the imaging position indication mark may of course be an arbitrary one. Further, the method of calculating the imaging position may also be an arbitrary one to replace the calculation method of the embodiment, and various changes and modifications are also allowed within a scope that does not depart from the spirit of the present invention.

According to the apparatus for obtaining visual images of cornea cells of the present invention as defined in claim 1, the view axis of a subject can be led from the center position to a required peripheral-position view target merely by selectively operating buttons or the like, which serve as switches, provided in the apparatus, and without requiring the decision of the operator. Thus, a magnified image of cornea cells of a required important site of an eyeball of a subject person can be easily observed or photographed.

According to the present invention as defined in claim 2, when the optical system of the imaging apparatus, after starting from its standby position, has reached an imaging position, the subject eye can be led correctly in a specified direction so that a visual image of the subject part can be obtained with high positional accuracy.

According to the present invention as defined in claim 3, in observing or photographing a magnified image of cornea cells of the subject part by leading the view axis of the subject person with the apparatus for obtaining visual images of cornea cells, a visual image of an important site where the cornea of the subject is stabilized can be obtained with simplicity.

According to the apparatus for obtaining visual images of cornea cells of the present invention as defined in claim 4, when a visual image at an imaging site of the cornea of the subject eye is obtained with the imaging site switchedly moved, the imaging direction is made perpendicular to a cornea surface such as the cornea endothelium surface of the imaging site or the cornea epithelium surface on which a contact lens is loaded, so that an eye-front image, in which the subject site where the light spot due to the alignment indicator light is positioned can be known, can be obtained while a magnified image of the cornea cells of the subject part can be obtained with high accuracy.

According to the method for displaying an imaging-position around a cornea for the apparatus for obtaining visual images of cornea cells of the present invention as defined in claim 5, in observing or photographing a magnified image of cornea endothelium cells of a subject part around the cornea, which is demanded depending on the contents of medical treatment, the imaging site, which would conventionally be displayed on the eye-front imaging screen only with an approximate, incorrect position, can now be known by displaying an imaging position mark at the correct position on the eyeball surface on the eye-front imaging screen, which can solve the conventional disadvantage and which largely contributes to medical treatment and examination of cornea endothelium.

What is claimed is:

1. An apparatus for obtaining visual images of cornea cells comprising:

an illumination optical system for illuminating through a slit an eyeball surface of a subject eye;

a magnification-imaging optical system for forming a magnified image of a subject part on an image receiving surface of a TV camera, based on slit illumination light with which the eyeball surface has been illuminated;

focusing-detection use receiving optics set in such a position as to receive cornea reflected light of the slit light via at least an objective lens;

an eye-front imaging optical system for obtaining a front image of the eye based on eye-front illumination light;

a plurality of view targets including a center view target set as opposed to the subject eye and composed of on-off switchable visible-light sources;

an alignment indicator light projection means for projecting alignment indicator light toward the subject eye;

a cornea-reflected-light receiving means for receiving cornea reflected light of the alignment indicator light;

a plurality of specified target points arranged on a photoreceptor of the reflected-light receiving means including a central target point and peripheral target points thereof, to one of which the cornea reflected light of the alignment indicator light chases; and a means for moving the imaging system relative to the subject eye depending on output from the light receiving means so that the cornea reflected light of the alignment indicator light is brought to one of the plurality of target points on the photoreceptor of the light receiving means, wherein each of said view targets corresponds to the respective target point on the photoreceptor and the reflected alignment indicator light chases the one of the plurality of target points when the corresponding view target is turned on.

2. An apparatus for obtaining visual images of cornea cells, comprising illumination means for flashing an eyeball surface of a patient eye through a slit-shaped aperture;

magnification optical means having an objective lens for enlarging slit-shaped visual images of a subject portion of the eyeball surface produced by the illumination means;

a video camera for obtaining the enlarged visual images of the subject portion of the eyeball surface produced by the magnification optical means;

a plurality of visible light sources provided in front of the eye, which includes a center target lamp and peripheral target lamps thereof; and switching means for switching on and off said target lamps one after another.

3. The apparatus for obtaining visual images of cornea cells according to claim 2, wherein said center target lamp is to be placed along an eye axis, which is a horizontal line axis passing through an eyeball rotational center; and said peripheral target lamps are radially arranged in directions of 4 o'clock, 6 o'clock, 8 o'clock, and 12 o'clock with respect to the center target lamp and are equally separated from the center target lamp.

4. The apparatus for obtaining visual images of cornea cells according to claim 2, wherein said center target lamp emits a target light along an optical axis of the video camera; and said peripheral target lamps are radially arranged in directions of 4 o'clock, 6 o'clock, 8 o'clock, and 12 o'clock with respect to the center target lamp and are equally separated from the center target lamp.

5. An apparatus for obtaining visual images of cornea cells, comprising an optical unit including (a) first optical means for observing and obtaining visual images of a frontal portion of a patient's eye via a video camera provided in front of the eye based of illumination lamps, (b) second optical means for flashing the eyeball surface through a slit-shaped aperture from a direction different from that of a first optical axis of the first optical means, (c) third optical means having an objective lens for enlarging slit-shaped visual images of a subject portion of the eyeball surface produced by the second optical means, (d) fourth optical means for sending out an alignment indicator light toward the eyeball surface along the first optical axis so that the indicator light is reflected back at a cornea surface of the eye, (e) a plurality of visible light sources provided in front of the eye, which includes a center target lamp and peripheral target lamps thereof, and (f) switching means for switching on and off said target lamps one after another;

reflected light receiving means having a light receiving element for receiving the reflected light of the alignment indicator light reflected at the cornea surface; and shifting means for shifting the optical unit in transverse and vertical directions in response to the alignment indicator light on the light receiving element of the light receiving means so that said reflected light moves towards a central prescribed position on the light receiving element, wherein said central prescribed position on the light receiving element is shiftable to one of a plurality of peripheral prescribed positions thereon in response to the on and off switching of the target lamps.

6. The apparatus for obtaining visual images of cornea cells according to claim 5, wherein said optical unit further comprises illumination means for illuminating the eyeball surface through a second slit from a direction of a second optical axis of the second optical means; and a receiving optics, which is provided along a fifth optical axis separated from a third optical axis of the third optical means, for detecting a focusing of the enlarged visual image of the subject portion of the cornea cells at a light receiving surface of the video camera when a focus of said enlarged visual image moves in front of the receiving optics as the optical unit is further shifted towards the eyeball after said reflected light on the light receiving element reached the prescribed position.

7. An apparatus for obtaining visual images of cornea cells, comprising: an optical unit including:

first optical means for observing and obtaining visual images of a frontal portion of a patient's eye via a video camera provided in front of the eye based on illumination lamps, second optical means for flashing the eyeball surface through a slit-shaped aperture from a direction different from that of a first optical axis of the first optical means, third optical means having an objective lens for enlarging slit-shaped visual images of a subject portion of the eyeball surface produced by the second optical means, fourth optical means for sending out an alignment indicator light toward the eyeball surface along the first optical axis so that the indicator light is reflected back at a cornea surface of the eye, a plurality of visible light sources provided in from of the eye, which include a center target lamp and peripheral target lamps thereof, reflected light receiving means having a light receiving element for receiving the reflected light of the alignment indicator light reflected at the cornea surface, and a plurality of prescribed target points arranged on the light receiving element of the reflected light receiving means including a central target point and peripheral target points thereof, to one of which the reflected alignment indicator light chases;

switching means for switching on and off said target lamps one after the other; and shifting means for shifting the optical unit in traverse and vertical directions in response to the alignment indicator light on the light receiving element of the light receiving means so that said reflected light moves towards one of the plurality of target points on the light receiving element;

wherein each of said target lamps corresponds to the respective target point on the light receiving element and the reflected alignment indicator light chases one of the plurality of target points when the corresponding target lamp is turned on.

8. The apparatus for obtaining visual images of corneas cells according to claim 7, wherein said optical unit further comprises:

illumination means for illuminating the eyeball surface through a second slit from a direction of a second optical axis of the second optical means; and a receiving optics, which is provided along a fifth optical axis extending from a third optical axis of the third optical means, for detecting a focusing of the enlarged visual image of the subject portion of the cornea cells formed at a light receiving surface of the video camera when a focus of said enlarged visual image moves in from of the receiving optics as the optical unit is further shifted towards the eyeball after said reflected alignment indicator light reached said one of the plurality of target points on the light receiving element.

* * * * *